(12) United States Patent
Itakura et al.

(10) Patent No.: US 10,039,698 B2
(45) Date of Patent: Aug. 7, 2018

(54) TOOTHPASTE COMPOSITION

(71) Applicant: KABUSHIKI KAISHA SANGI, Tokyo (JP)

(72) Inventors: Takayuki Itakura, Tokyo (JP); Rimiko Takikawa, Tokyo (JP); Mariko Obuki, Tokyo (JP); Rie Takamatsu, Tokyo (JP)

(73) Assignee: KABUSHIKI KAISHA SANGI, Tokyo (JP)

( * ) Notice: Subject to any disclaimer, the term of this patent is extended or adjusted under 35 U.S.C. 154(b) by 0 days.

(21) Appl. No.: 15/510,648

(22) PCT Filed: Jan. 14, 2016

(86) PCT No.: PCT/JP2016/000154
§ 371 (c)(1),
(2) Date: Mar. 10, 2017

(87) PCT Pub. No.: WO2016/114137
PCT Pub. Date: Jul. 21, 2016

(65) Prior Publication Data
US 2017/0189287 A1     Jul. 6, 2017

(30) Foreign Application Priority Data
Jan. 16, 2015   (JP) .................. 2015-006938

(51) Int. Cl.
*A61Q 11/00*     (2006.01)
*A61K 8/24*       (2006.01)
*A61K 8/92*       (2006.01)

(52) U.S. Cl.
CPC .............. *A61K 8/24* (2013.01); *A61K 8/92* (2013.01); *A61K 8/922* (2013.01); *A61K 8/925* (2013.01); *A61K 8/927* (2013.01); *A61Q 11/00* (2013.01)

(58) Field of Classification Search
CPC ..................................................... A61Q 11/00
USPC .......................................................... 424/57
See application file for complete search history.

(56) References Cited

U.S. PATENT DOCUMENTS

| 5,037,639 | A | 8/1991 | Tung |
| 5,833,959 | A | 11/1998 | Atsumi et al. .................. 424/57 |
| 2001/0007652 | A1 | 7/2001 | Takeda et al. |
| 2005/0025721 | A1* | 2/2005 | Holme ................. A23G 3/36 424/48 |

FOREIGN PATENT DOCUMENTS

| JP | 07-223930 | 8/1995 |
| JP | 8-310929 | 11/1996 |
| JP | 9-202717 | 8/1997 |
| JP | 10-001427 | 1/1998 |
| JP | 10-59814 | 3/1998 |
| JP | 11-21219 | 1/1999 |
| JP | 11-349461 | 12/1999 |
| JP | 2000-128752 | 5/2000 |
| JP | 2000-143469 | 5/2000 |
| JP | 2001-122748 | 5/2001 |
| JP | 2001-122750 | 5/2001 |
| JP | 2001-302428 | 10/2001 |
| JP | 2002-020254 | 1/2002 |
| JP | 2002-114657 | 4/2002 |
| JP | 2004-018521 | 1/2004 |
| JP | 2005-314266 | 11/2005 |
| JP | 2006-213668 | 8/2006 |
| JP | 2007-99632 | 4/2007 |
| JP | 2011-144160 | 7/2011 |
| JP | 2014-73989 | 4/2014 |
| WO | 2013/181479 | 12/2013 |

OTHER PUBLICATIONS

Notification of Transmittal of Translation of the International Preliminary Report on Patentability dated Jul. 27, 2017, for International Application No. PCT/JP2016/000154, and the English translation of the International Preliminary Report on Patentability, 12 pages.
Extended European Search Report for European Application No. 16737208.5 issued by the European Patent Office dated May 14, 2018, 6 pages.

* cited by examiner

*Primary Examiner* — Nannette Holloman
(74) *Attorney, Agent, or Firm* — Occhiuti & Rohlicek LLP

(57) ABSTRACT

An object of the present invention is to provide a tooth-cleaning composition having a high remineralizing effect on demineralized dental enamel. The tooth-cleaning composition contains a wax and a calcium phosphate, wherein a content of the calcium phosphate is 0.001 to 33% by mass.

5 Claims, 2 Drawing Sheets

[Figure 1]
EXAMPLE 20
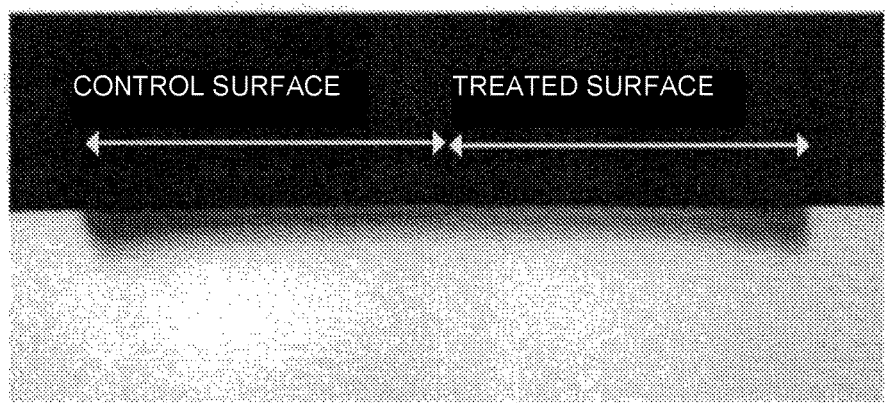
[Figure 2]
EXAMPLE 58
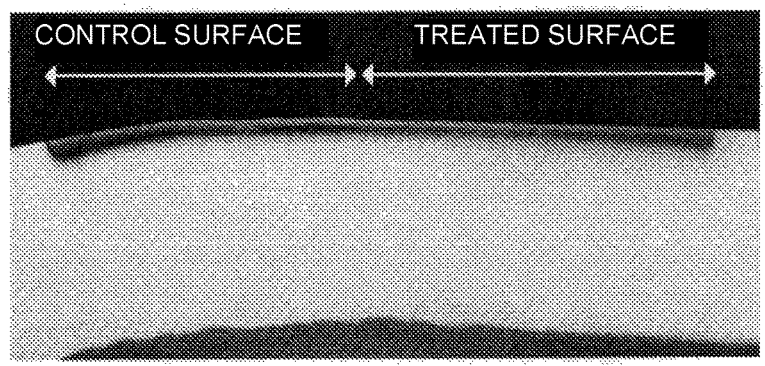

TOOTHPASTE COMPOSITION

CROSS REFERENCE TO RELATED APPLICATIONS

This application is a National Stage of International Application No. PCT/JP2016/000154 filed on Jan. 14, 2016, which claims priority to Japanese Application No. 2015-006938 filed on Jan. 16, 2015, the contents of which are hereby incorporated by reference in their entirety.

TECHNICAL FIELD

The present invention relates to a tooth-cleaning composition having a tooth-remineralizing effect.

BACKGROUND ART

Caries begins with the adhesion of tooth decay bacteria, such as *Streptococcus mutans*, to the tooth surface for the formation of dental plaque, and organic acids produced by food metabolism by the tooth decay bacteria in the dental plaque demineralize dental enamel to cause an incipient caries condition. Saliva remineralizes the demineralized part through the action of calcium and phosphorous in the saliva and thereby serves to return the tooth to the original condition. If the remineralization can sufficiently regenerate the demineralized tooth, the occurrence of caries can be suppressed.

Accordingly, dentifrices containing a fluoride, or hydroxyapatite, one of calcium phosphates, having a crystal structure similar to the inorganic component of tooth, to promote the remineralization of the tooth are manufactured and distributed.

However, the saliva or the use a dentifrice containing a fluoride or hydroxyapatite is not sufficient for the remineralization of the demineralized part, and there is a need for the development of oral compositions, such as a dentifrice, capable of sufficiently achieving the remineralization.

Accordingly, there are proposed an oral dentifrice containing hydroxyapatite or tricalcium phosphate having a particle diameter of 0.05 μm to 1.0 μm which is capable of repairing minute asperities on the tooth surface, protecting the tooth surface, preventing tooth decay, strengthening dentin, and having an enhanced whitening effect (Patent Document 1), an oral composition capable of allowing hydroxyapatite fine powder to long reside on the tooth surface by the incorporation of the hydroxyapatite fine powder in a water-soluble cellulose solution (Patent Document 2), an oral composition capable of remarkably promoting remineralization through the combined use of a sugar alcohol, such as xylitol, and dibasic calcium phosphate (Patent Document 3), an oral composition containing low-crystallinity hydroxyapatite which is capable of preventing disease and unpleasant feelings in oral cavity by adhering to oral bacteria for bacteria elimination (Patent Document 4), an oral composition containing a calcium compound, such as hydroxyapatite, in royal jelly or its extract which is capable of whitening teeth, preventing tooth decay through remineralization, and preventing periodontal disease (Patent Document 5), a tooth-cleaning composition containing a calcium compound, such as hydroxyapatite, in an ultramarine composition which is capable of having a promoted tooth-remineralizing effect (Patent Document 6), a remineralization promoter having an anti-caries function, containing a micellar calcium phosphate-phosphopeptide complex (Patent Document 7), a method capable of promoting remineralization and suppressing caries by washing teeth using a dentifrice containing fluoride ions and then allowing an oral liquid composition containing calcium ions to act thereon (Patent Document 8), a tooth-cleaning composition having a pH of 5 to 8 and containing tricalcium phosphate as a powdered calcium salt having the ability to convert to hydroxyapatite by contacting with water in oral cavity (Patent Document 9), and the like.

To promote remineralization, a chewing gum and the like containing xylitol, and calcium phosphate, noncrystalline calcium phosphate, or calcium phosphoryl oligosaccharide are also manufactured; however, they are not necessarily sufficient in remineralization.

On the other hand, there are proposed tooth-cleaning compositions capable of imparting gloss to teeth by containing wax (Patent Documents 10 and 11), a method for improving the astringency of an oral composition containing an astringent compound (Patent Document 12), a method for suppressing the occurrence of astringency and metallic taste by incorporating wax in a tooth-cleaning composition having astringency and metallic taste (Patent Document 13), and the like. Wax is present on the surface of animal and plant bodies, often acts as a protective coat, and is used for grazing in cosmetics and pharmaceutical products and the like after purification; however, it has no tooth-remineralizing action.

PRIOR ART DOCUMENTS

Patent Documents

Patent Document 1
Japanese unexamined Patent Application Publication No. 09-202717
Patent Document 2
Japanese unexamined Patent Application Publication No. 10-59814
Patent Document 3
Japanese unexamined Patent Application Publication No. 2000-128752
Patent Document 4
Japanese unexamined Patent Application Publication No. 2001-122748
Patent Document 5
Japanese unexamined Patent Application Publication No. 2005-314266
Patent Document 6
Japanese unexamined Patent Application Publication No. 2014-73989
Patent Document 7
Japanese unexamined Patent Application Publication No. 2006-213668
Patent Document 8
Japanese unexamined Patent Application Publication No. 2007-99632
Patent Document 9
Japanese unexamined Patent Application Publication No. 07-223930
Patent Document 10
Japanese unexamined Patent Application Publication No. 08-310929
Patent Document 11
Japanese unexamined Patent Application Publication No. 2000-143469
Patent Document 12
Japanese unexamined Patent Application Publication No. 11-21219
Patent Document 13
Japanese unexamined Patent Application Publication No. 11-349461

SUMMARY OF THE INVENTION

Object to be Solved by the Invention

An object of the present invention is to provide a tooth-cleaning composition having a high remineralizing effect on demineralized dental enamel.

Means to Solve the Object

As a result of intensive studies for solving the above-described problems, the present inventors have found that incorporation of wax, conventionally only known to have the effect of imparting gloss and luster and the effect of improving astringency and not having, by itself, a remineralization action, together with a calcium phosphate, such as hydroxyapatite, tricalcium phosphate, and calcium monohydrogen phosphate, in a tooth-cleaning composition remarkably enhances its tooth-remineralizing effect, thereby accomplishing the present invention.

Specifically, the present invention is specified by matters provided below.
(1) A tooth-cleaning composition comprising a wax and a calcium phosphate, wherein a content of the calcium phosphate is 0.001 to 33% by mass.
(2) The tooth-cleaning composition according to "1", wherein the content of the wax is 0.0001 to 30% by mass.
(3) The tooth-cleaning composition according to "1" or "2", wherein the calcium phosphate is at least one selected from the group consisting of hydroxyapatite, tricalcium phosphate, and calcium monohydrogen phosphate.
(4) The tooth-cleaning composition according to any one of "1" to "3", wherein the wax is at least one selected from the group consisting of shellac wax, Wang Li Guro, carnauba wax, sugar cane wax, bleached beeswax, bleached montan wax, rice bran wax, hydrogenated rice bran wax, spermaceti, deresin candelilla wax, candelilla wax, montan wax, paraffin wax, microcrystalline wax, Japan wax, oil seed wax, lanolin, beeswax, Chinese insect wax, and cane wax.
(5) The tooth-cleaning composition according to any one of "1" to "4", wherein the composition is a toothpaste, a toothpowder, or a liquid dentifrice.

Effect of the Invention

The tooth-cleaning composition of the present invention enables a remarkably enhancement in the remineralizing effect of a calcium phosphate. Thus, the tooth-cleaning composition of the present invention is excellent in the remineralization of demineralized dental enamel and can provide an excellent remineralizing effect even with a decreased content of the calcium phosphate.

BRIEF DESCRIPTION OF DRAWINGS

FIG. 1 is a photograph showing the control and treated surfaces of a coronal portion in Example 20 using a contact micro radiogram (CMR).

FIG. 2 is a photograph showing the control and treated surfaces of a coronal portion in Example 58 using a contact micro radiogram (CMR).

MODE OF CARRYING OUT THE INVENTION

Figure 3:
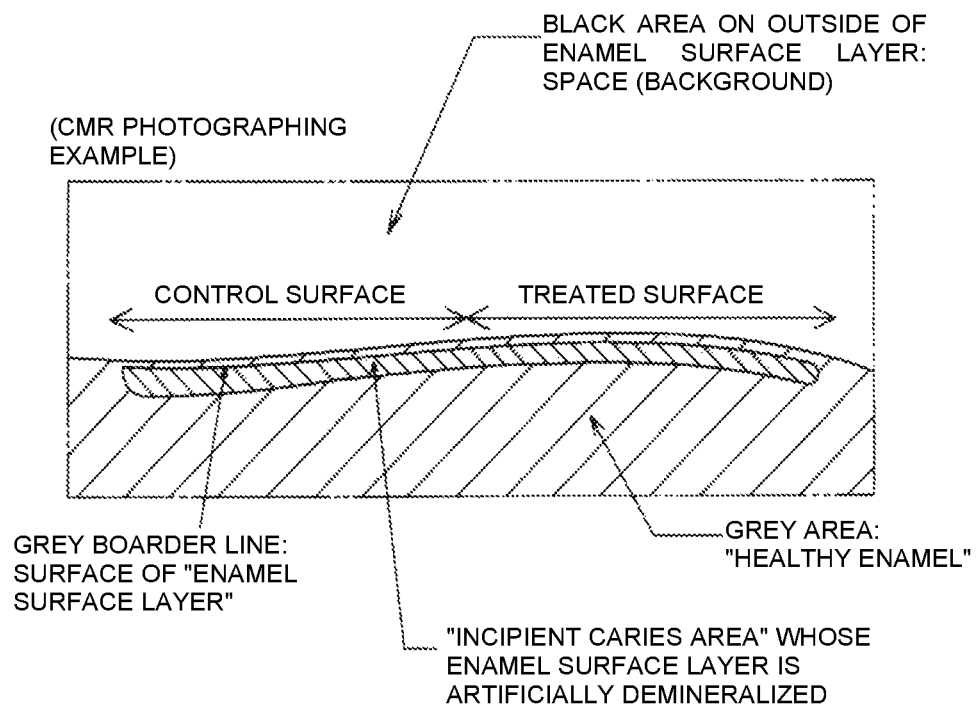
FIG. 3 is a diagram obtained by drawing the photographs shown in FIGS. 1 and 2 using kozumi (deep Sumi Japanese ink) and adding an explanation of the state of each part.

The tooth-cleaning composition of the present invention is not particularly limited provided that the composition contains a wax and a calcium phosphate and has a content of the calcium phosphate of 0.001 to 33% by mass; specific examples thereof can include a toothpaste, a toothpowder, or a liquid dentifrice. The calcium phosphate according to the present invention is not particularly limited provided that it is a calcium salt of phosphoric acid; examples thereof can include hydroxyapatite, tricalcium phosphate, and calcium monohydrogen phosphate; and these calcium phosphates may be used alone or in a combination of two or more thereof and may be hydrates thereof or those whose phosphorus and calcium are partly substituted by other elements, such as magnesium, zinc, titanium, sodium, and potassium. The calcium phosphate according to the present invention is preferably at least one selected from the group consisting of hydroxyapatite, tricalcium phosphate, and calcium monohydrogen phosphate in view of promoting remineralization.

Hydroxyapatite as one of the calcium phosphates according to the present invention may be one obtained from bones of food fishes, such as salmon, pig bones, beef bones, and the like as natural hard tissues in addition to one synthesized by a conventional method. Typically, hydroxyapatite is stoichiometrically represented by the composition of $Ca_{10}(PO_4)_6(OH)_2$; however, the Ca/P molar ratio being not 1.67, which is non-stoichiometric, can also result in the exhibition of properties of hydroxyapatite and the assumption of an apatite structure. For example, a synthetic hydroxyapatite having a Ca/P molar ratio of on the order of 1.4 to 1.8 is also encompassed in the hydroxyapatite according to the present invention.

The hydroxyapatite used in the present invention may be crystalline, low-crystalline, or noncrystalline; however, it is preferably low-crystalline or noncrystalline hydroxyapatite in view of a caries-preventing effect (hereinafter, the low-crystalline hydroxyapatite and the noncrystalline hydroxyapatite are referred to as "amorphous hydroxyapatite"). "Low-crystallinity" refers to crystallinity for which the X-ray diffraction peak is broad compared to that of high-crystalline powder, and "noncrystallinity" refers to crystallinity for which the X-ray diffraction pattern has a broad halo pattern and no diffraction pattern showing the character of a crystal is obtained. Such amorphous hydroxyapatite can be obtained, for example, by drying apatite synthesized by a wet synthesis method by lyophilization or drying at a temperature of 100° C. or lower or by baking at a temperature of on the order of 300° C. or lower.

The content of hydroxyapatite in the tooth-cleaning composition of the present invention is 0.001 to 33% by mass based on the whole tooth-cleaning composition and is preferably 0.001 to 30% by mass, more preferably 0.01 to 20% by mass, still more preferably 0.1 to 20% by mass, based on the whole tooth-cleaning composition, in view of the remineralizing effect and sense of use thereof.

Tricalcium phosphate as one of the calcium phosphates according to the present invention is also referred to as tribasic calcium phosphate, has the composition represented by the chemical formula: $Ca_3(PO_4)_2$, and is widely commonly used in pharmaceutical products and cosmetics as well as foods, sundry articles, the petrochemical industry, and the like. Examples of tricalcium phosphate used in the present invention include, but not limited to, a product conforming to the standards, such as Japanese Pharmaceutical Excipients, Japanese Standards of Quasi-drug Ingredients, and Japanese Cosmetic Ingredients Codex.

Calcium monohydrogen phosphate as one of the calcium phosphates according to the present invention is also referred to as dibasic calcium phosphate, has the composition represented by the chemical formula: $CaHPO_4$ or CaHPO$_4$.2H$_2$O as its dehydrate, and is widely commonly used in pharmaceutical products, foods, cosmetics, industrial raw materials, and the like. Examples of calcium monohydrogen phosphate include, but not limited to, a product conforming to the standards, such as Japanese Standards and Criteria for Food and Food Additives, Japanese Pharmacopeia, and Japanese Standards of Quasi-drug Ingredients.

The contents of tricalcium phosphate and calcium monohydrogen phosphate according to the present invention are 0.001 to 33% by mass based on the whole tooth-cleaning composition and are preferably 0.001 to 30% by mass, more preferably 0.01 to 20% by mass, still more preferably 0.1 to 20% by mass, based on the whole tooth-cleaning composition, in view of the remineralizing effect and sense of use thereof.

Wax is an ester consisting typically of a higher fatty acid and a monohydric or dihydric higher alcohol, is solid or liquid and resembles fat and oil, but is stable to oxidation and hydrolysis. Customarily, wax also includes substances not falling within the above definition, for example, sekiro (in Japanese) as another name of the hydrocarbon paraffin, and Japan wax, almost consisting of fat. Wax is classified into liquid wax and solid wax, and solid wax is divided into plant wax and animal wax. Here, examples of the plant wax include carnauba wax, candelilla wax, rice bran wax, Japan wax, and sucrose wax, and examples of the animal wax include beeswax, spermaceti, and Chinese white insect wax. The wax according to the present invention refers to wax in the conventional broader sense.

The wax according to the present invention is not particularly limited; preferred examples thereof can include shellac wax, Wang Li Guro, carnauba wax, sugar cane wax, bleached beeswax, bleached montan wax, rice bran wax, hydrogenated rice bran wax, spermaceti, deresin candelilla wax, candelilla wax, montan wax, paraffin wax, microcrystalline wax, Japan wax, oil seed wax, lanolin, beeswax, Chinese insect wax, cane wax, sucrose wax, and Chinese white insect wax. Among them, carnauba wax, candelilla wax, rice bran wax, beeswax, and Japan wax are preferable exemplified. These waxes may be used alone or in a combination of two or more thereof.

Carnauba wax is a natural wax extracted from a type of palm. Carnauba wax used in the present invention may be a pale yellow to light brown one; specific examples thereof can include Special Carnauba Wax 1 from S. Kato & Co., Cerarica carnauba wax from CERARICA NODA Co., Ltd., Polishing Wax-105 from Freund Industrial Co., Ltd.

Candelilla wax is a natural wax obtained from the stem of candelilla grass. Candelilla wax used in the present invention may be a pale yellow to light brown one; specific examples thereof can include purified candelilla wax MK-4 from Yokoseki Oil & Fat Industries Co., Ltd., Cerarica Candelilla Wax from CERARICA NODA Co., Ltd., Miki Chemical Industry & Co., Ltd., and Yamakei Sangyo Co., Ltd., and purified candelilla wax Toku-go from Cerica Noda Co., Ltd.

Examples of the waxes used in the present invention include, but not limited to, a product conforming to standards, such as Standards of the Japanese Pharmacopoeia, Japanese Standards and Criteria for Food and Food Additives, Japanese Standards of Cosmetic Ingredients, and Japanese Standards of Quasi-drug Ingredients.

The amount of wax incorporated according to the present invention is not particularly limited; however, it is preferably 0.0001 to 30% by mass, more preferably 0.001 to 20% by mass, still more preferably 0.01 to 10% by mass, yet more preferably 0.01 to 5% by mass, based on the whole tooth-cleaning composition, in view of the promoting effect for remineralization and sense of use thereof. According to the present invention, the tooth-cleaning composition contains a wax in addition to a calcium phosphate, which can remarkably enhance its remineralizing effect compared to that for the calcium phosphate alone. Thus, the tooth-cleaning composition of the present invention is excellent in the remineralization of demineralized dental enamel. A decreased content of a calcium phosphate can provide a remineralizing effect similar to or more than that by a high content of the calcium phosphate; thus, the calcium phosphate content in the tooth-cleaning composition can be decreased, if necessary, from the standpoint of improving sense of use and the relationship with other ingredients to be incorporated.

The tooth-cleaning composition of the present invention may contain additives, such as an abrasive, a thickener, and a binder, commonly used in a tooth-cleaning composition, a wetting agent, a foaming agent, a perfume, a sweetener, a preservative, and various active ingredients, in addition to the above-described components. Specific examples of these components are shown below. In addition to the components shown below, proper components may be further incorporated depending on the purpose thereof, the type of the composition, and the like.

Examples of the abrasive can include calcium carbonate, calcium pyrophosphate, silica such as abrasive precipitated silica or abrasive gel silica, calcium silicate, aluminum silicate, aluminum oxide, aluminum hydroxide, alumina, zeolite, titanium oxide, zirconium silicate, insoluble sodium metaphosphate, trimagnesium phosphate, magnesium carbonate, calcium sulfate, magnesium sulfate, polymethyl methacrylate, bentonite, and synthetic resin.

Examples of the thickener can include hydroxyethylcellulose, sodium carboxymethylcellulose, carrageenan, carboxyvinyl polymer, xanthan gum, gelatin, pullulan, sodium alginate, sodium polyacrylate, polyvinyl alcohol, locust bean gum, guar gum, and hydroxypropylmethylcellulose.

Examples of the binder can include methyl cellulose, propylene glycol alginate, pullulan, tragacanth gum, xanthan gum, pectin, Furcelleran, chitosan, polyethylene oxide, polyvinyl pyrrolidone, polyacrylic acid, polymethacrylic acid, peptone, casein, collagen, albumin, gum arabic, karaya gum, Eudragit, ethyl cellulose, cellulose acetate, sodium polyacrylate, polyvinyl alcohol, polyvinyl acetal-dimethylamino acetate, and cellulose acetate-dibutylhydroxypropyl ether.

Examples of the emulsifier can include polyoxyethylene hydrogenated castor oil, sorbitan monostearate, glycerin fatty acid ester, propylene glycol fatty acid ester, alkyl glyceryl ether, polyoxyethylene sorbitol fatty acid ester, polysorbate, polyoxyethylene, lauromacrogol, sodium alkyl sulfate, alkyl phosphate ester, sodium alkylbenzene sulfonate, sodium N-acylsarcosinate, N-acylglutaminate, sucrose fatty acid ester, an alkyl glycoside, alkyl dimethyl amine oxide, and an alkyl betaine.

Examples of the fat and oil component can include liquid paraffin, a higher alcohol such as cetyl alcohol and stearyl alcohol, a fatty acid ester such as isopropyl myristate, lanolin, a fatty acid, an ester compound such as octyldodecyl myristate, diisopropyl adipate, hexadecyl isostearate, and decyl oleate, squalane, squalene, a medium chain fatty acid triglyceride, and silicone.

Examples of the alcohol can include a lower alcohol such as ethanol, propyl alcohol, isopropyl alcohol, butanol, and isobutanol and a polyhydric alcohol such as ethylene glycol, diethylene glycol, propylene glycol, dipropylene glycol, 1,3-butylene glycol, glycerin, 1,5-pentanediol, sorbit, and polyethylene glycol.

Examples of the surfactant can include: a nonionic surfactant, such as sorbitan fatty acid ester, glycerin fatty acid ester, decaglycerin fatty acid ester, polyglycerin fatty acid ester, decaglyceryl laurate, propylene glycol-pentaerythritol fatty acid ester, polyoxyethylene sorbitan fatty acid ester, polyoxyethylene glycerin fatty acid ester, polyoxyethylene sorbit fatty acid ester, polyethylene glycol fatty acid ester, sucrose fatty acid ester, polyoxyethylene alkyl ether, polyoxyethylene polyoxypropylene glycol, polyoxypropylene alkyl ether, polyoxyethylene polyoxypropylene alkyl ether, polyoxyethylene alkyl phenyl ether, polyoxyethylene castor oil-hydrogenated castor oil, polyoxyethylene lanolin-lanolin alcohol-bees wax derivative, polyoxyethylene alkyl amine-fatty acid amide, polyoxyethylene alkylphenyl formaldehyde condensate, and homogeneous polyoxyethylene alkyl ether; an anionic surfactant, such as sodium lauryl sulfate, sodium myristyl sulfate, alkyl sulfate, polyoxyethylene alkyl sulfate, N-acylamino acid or a salt thereof, N-acyl methyl taurine or a salt thereof, polyoxyethylene alkyl ether acetate, alkyl sulfo carboxylate, α-olefin sulfonate, alkyl phosphate, or polyoxyethylene alkyl ether phosphate; a cationic surfactant, such as alkyl ammonium and alkyl benzyl ammonium salt; and an amphoteric surfactant, such as betaine acetate, imidazolinium betaine, and lecithin.

Examples of the pH adjustor can include: citric acid and a salt thereof, phosphoric acid and a salt thereof, malic acid and a salt thereof, gluconic acid and a salt thereof, maleic acid and a salt thereof, aspartic acid and a salt thereof, gluconic acid and a salt thereof, succinic acid and a salt thereof, glucuronic acid and a salt thereof, fumaric acid and a salt thereof, glutamic acid and a salt thereof, and adipic acid and a salt thereof; an inorganic acid such as hydrochloric acid; hydrofluoric acid; an alkali metal hydroxide such as sodium hydroxide and potassium hydroxide; and an amine such as triethanolamine, diethanolamine, and diisopropanolamine.

Examples of the stabilizer can include: vitamin C, vitamin E, and a salt thereof; sodium sulfite, sodium pyrosulfite, sodium bisulfite, butylated hydroxytoluene, dibutylated hydroxytoluene, butylated hydroxyanisole, edetic acid or a salt thereof.

Examples of the wetting agent can include a polyhydric alcohol, such as glycerin, propylene glycol, polyethylene glycol, sorbitol, xylitol, ethylene glycol, 1,3-butylene glycol, and isopropylene glycol.

Examples of the foaming agent can include sodium lauryl sulfate, N-lauroyl sarcosine sodium, and a nonionic surfactant.

Examples of the perfume can include an essential oil, such as menthol, peppermint, and spearmint, eucalyptus oil, orange oil, lemon oil, Wynn Dah green oil, clove oil, mint oil, thyme oil, sage oil, carvone, linalool, eugenol, anethole, and herb mint.

Examples of the sweetener can include saccharin sodium, aspartame, stevioside, neohesperidyl dihydrochalcone, glycyrrhizin, aspartyl phenylalanine methyl ester, acesulfame potassium, perillartine, p-methoxy cinnamic aldehyde, and xylitol.

Examples of the preservative can include p-hydroxybenzoic ester, alkyldiaminoethylglycine hydrochloride, methylparaben, ethylparaben, and sodium benzoate.

Examples of other medicinal components can include allantoin, tocopherol acetate, isopropyl phenol, triclosan, chlorhexidine, chlorophyll, flavonoid, tranexamic acid, hinokitiol, cetylpyridinium chloride, sodium fluoride, stannous fluoride, sodium monofluorophosphate, dextranase, mutanase, protease, aminocaproic acid, glycyrrhizic acid, glycyrrhetinic acid, azulene, allantoin, lysozyme chloride, cork tree bark extract, a polyphosphoric acid, and sodium chloride.

The amounts of these optional components incorporated are properly used in a pharmaceutically acceptable range not impeding the effect of the invention. The tooth-cleaning composition of the present invention can be produced by a conventional method for producing tooth-cleaning compositions, such as a toothpaste, a toothpowder, and a liquid dentifrice. In the production of the tooth-cleaning composition of the present invention, a wax, a calcium phosphate, such as hydroxyapatite, tricalcium phosphate, or calcium monohydrogen phosphate, and other components may be added in any step of the production process.

EXAMPLES

Toothpastes (Examples 1 to 123) and liquid dentifrice (Examples 124 to 135) in each of which any of various wax compositions and hydroxyapatite, tricalcium phosphate, or calcium monohydrogen phosphate were incorporated were prepared and subjected to a remineralization test.

[Wax Composition]

Each wax composition used was carnauba wax (Polishing Wax-105 from Freund Industrial Co., Ltd.), candelilla wax (purified candelilla wax Toku-go from Cerica NODA Co., Ltd.), rice bran wax (NC-1720 from Cerica Noda Co., Ltd.), beeswax (deodorized purified beeswax High acid from Cerica Noda Co., Ltd.), or Japan wax (Japan wax-100 from Cerica Noda Co., Ltd.).

[Hydroxyapatite]

A phosphoric acid aqueous solution having a concentration of 30% by mass was dropwise added to a calcium hydroxide suspension under stirring until pH 10 was achieved, and the formed gelled substance was matured by standing at room temperature for 1 day. Thereafter, the gelled substance was filtered using a glass filter, and the remaining substance was dried in the air at 100° C. to provide hydroxyapatite powder. The resultant hydroxyapatite powder had a maximum particle diameter of about 40 µm, a minimum particle diameter of about 0.05 µm, and an average particle diameter of about 5 µm. This hydroxyapatite powder was used.

[Tricalcium Phosphate]

Tricalcium phosphate used was Tricalcium Phosphate (a food additive from Taihei Chemical Industrial Co. Ltd.).

[Calcium Monohydrogen Phosphate (Dibasic Calcium Phosphate)]

Calcium monohydrogen phosphate used was Calcium Hydrogen Phosphate (a food additive from Yoneyama Chemical Industry Co., Ltd.).

For Comparative Examples, toothpastes and liquid dentifrices in each of which any of various wax compositions, and hydroxyapatite, tricalcium phosphate, or calcium monohydrogen phosphate were incorporated were prepared and subjected to a remineralization test.

1. Toothpaste

TABLE 1

|  | Example 1 | Example 2 | Example 3 | Example 4 | Example 5 | Example 6 |
| --- | --- | --- | --- | --- | --- | --- |
| Carnauba Wax | 30.0 | 0.0001 | — | — | — | — |
| Candelilla Wax | — | — | 30.0 | 0.0001 | — | — |
| Rice Bran Wax | — | — | — | — | 0.001 | — |
| Beeswax | — | — | — | — | — | 20.0 |
| Japan Wax | — | — | — | — | — | — |
| Hydroxyapatite | 30.0 | 30.0 | 30.0 | 30.0 | 30.0 | 30.0 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 2

|  | Example 7 | Example 8 | Example 9 | Example 10 | Example 11 | Example 12 |
| --- | --- | --- | --- | --- | --- | --- |
| Carnauba Wax | — | 20.0 | — | — | 2.0 | — |
| Candelilla Wax | — | — | 0.2 | — | — | 10.0 |
| Rice Bran Wax | — | — | — | — | — | — |
| Beeswax | — | — | — | 5.0 | — | — |
| Japan Wax | 30.0 | — | — | — | — | — |
| Hydroxyapatite | 30.0 | 20.0 | 20.0 | 20.0 | 10.0 | 10.0 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 3

|  | Example 13 | Example 14 | Example 15 | Example 16 | Example 17 | Example 18 |
| --- | --- | --- | --- | --- | --- | --- |
| Carnauba Wax | — | — | — | 30.0 | 10.0 | 5.0 |
| Candelilla Wax | — | — | — | — | — | — |
| Rice Bran Wax | 30.0 | — | — | — | — | — |
| Beeswax | — | 0.0001 | — | — | — | — |
| Japan Wax | — | — | 2.0 | — | — | — |
| Hydroxyapatite | 10.0 | 10.0 | 10.0 | 5.0 | 5.0 | 5.0 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |

TABLE 3-continued

|  | Example 13 | Example 14 | Example 15 | Example 16 | Example 17 | Example 18 |
| --- | --- | --- | --- | --- | --- | --- |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 4

|  | Example 19 | Example 20 | Example 21 | Example 22 | Example 23 | Example 24 |
| --- | --- | --- | --- | --- | --- | --- |
| Carnauba Wax | 0.2 | 0.02 | 0.0001 | — | — | — |
| Candelilla Wax | — | — | — | 20.0 | 2.0 | 0.2 |
| Rice Bran Wax | — | — | — | — | — | — |
| Beeswax | — | — | — | — | — | — |
| Japan Wax | — | — | — | — | — | — |
| Hydroxyapatite | 5.0 | 5.0 | 5.0 | 5.0 | 5.0 | 5.0 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 5

|  | Example 25 | Example 26 | Example 27 | Example 28 | Example 29 | Example 30 |
| --- | --- | --- | --- | --- | --- | --- |
| Carnauba Wax | — | — | — | — | — | — |
| Candelilla Wax | 0.001 | — | — | — | — | — |
| Rice Bran Wax | — | 2.0 | 0.2 | — | — | — |
| Beeswax | — | — | — | 2.0 | 0.2 | — |
| Japan Wax | — | — | — | — | — | 0.2 |
| Hydroxyapatite | 5.0 | 5.0 | 5.0 | 5.0 | 5.0 | 5.0 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 6

|  | Example 31 | Example 32 | Example 33 | Example 34 | Example 35 | Example 36 |
|---|---|---|---|---|---|---|
| Carnauba Wax | — | 0.001 | — | — | — | — |
| Candelilla Wax | — | — | 5.0 | 0.02 | — | — |
| Rice Bran Wax | — | — | — | — | 0.0001 | — |
| Beeswax | — | — | — | — | — | 30.0 |
| Japan Wax | 0.02 | — | — | — | — | — |
| Hydroxyapatite | 5.0 | 1.0 | 1.0 | 1.0 | 1.0 | 1.0 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 7

|  | Example 37 | Example 38 | Example 39 | Example 40 | Example 41 | Example 42 |
|---|---|---|---|---|---|---|
| Carnauba Wax | — | 10.0 | — | — | 0.2 | — |
| Candelilla Wax | — | — | 2.4 | — | — | 20.0 |
| Rice Bran Wax | — | — | — | 5.0 | — | — |
| Beeswax | — | — | — | — | — | — |
| Japan Wax | 0.0001 | — | — | — | — | — |
| Hydroxyapatite | 1.0 | 0.1 | 0.1 | 0.1 | 0.01 | 0.01 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 8

|  | Example 43 | Example 44 | Example 45 | Example 46 | Example 47 | Example 48 |
|---|---|---|---|---|---|---|
| Carnauba Wax | — | 30.0 | 0.0001 | — | — | — |
| Candelilla Wax | — | — | — | 30.0 | 0.0001 | — |
| Rice Bran Wax | — | — | — | — | — | 0.02 |
| Beeswax | — | — | — | — | — | — |
| Japan Wax | 5.0 | — | — | — | — | — |
| Hydroxyapatite | 0.01 | 0.001 | 0.001 | 0.001 | 0.001 | 0.001 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |

TABLE 8-continued

|  | Example 43 | Example 44 | Example 45 | Example 46 | Example 47 | Example 48 |
| --- | --- | --- | --- | --- | --- | --- |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 9

|  | Example 49 | Example 50 | Example 51 | Example 52 | Example 53 |
| --- | --- | --- | --- | --- | --- |
| Carnauba Wax | — | — | 0.01 | 0.1 | — |
| Candelilla Wax | — | — | 0.01 | — | 0.5 |
| Rice Bran Wax | — | — | — | 0.1 | 0.5 |
| Beeswax | 10.0 | — | — | — | 0.5 |
| Japan Wax | — | 0.001 | — | — | 0.5 |
| Hydroxyapatite | 0.001 | 0.001 | 5.0 | 5.0 | 5.0 |
| Glycerin | 20.0 | 20.0 | 20.0 | 20.0 | 20.0 |
| Carboxymethyl Cellulose | 2.0 | 2.0 | 2.0 | 2.0 | 2.0 |
| Silica | 5.0 | 5.0 | 5.0 | 5.0 | 5.0 |
| Polyethylene Glycol | 3.0 | 3.0 | 3.0 | 3.0 | 3.0 |
| Sodium Lauryl Sulfate | 1.0 | 1.0 | 1.0 | 1.0 | 1.0 |
| Cetylpyridinium Chloride | 0.1 | 0.1 | 0.1 | 0.1 | 0.1 |
| Menthol | 0.5 | 0.5 | 0.5 | 0.5 | 0.5 |
| Purified Water | Balance | Balance | Balance | Balance | Balance |
| Total | 100.0 | 100.0 | 100.0 | 100.0 | 100.0 |

TABLE 10

|  | Example 54 | Example 55 | Example 56 | Example 57 | Example 58 | Example 59 |
| --- | --- | --- | --- | --- | --- | --- |
| Carnauba Wax | 30.0 | — | — | 2.0 | — | — |
| Candelilla Wax | — | 0.0001 | — | — | 10.0 | — |
| Rice Bran Wax | — | — | 5.0 | — | — | 30.0 |
| Beeswax | — | — | — | — | — | — |
| Japan Wax | — | — | — | — | — | — |
| Tricalcium Phosphate | 30.0 | 30.0 | 30.0 | 10.0 | 10.0 | 10.0 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 11

|  | Example 60 | Example 61 | Example 62 | Example 63 | Example 64 | Example 65 |
|---|---|---|---|---|---|---|
| Carnauba Wax | — | — | 10.0 | 0.2 | 0.02 | 0.0001 |
| Candelilla Wax | — | — | — | — | — | — |
| Rice Bran Wax | — | — | — | — | — | — |
| Beeswax | 0.0001 | — | — | — | — | — |
| Japan Wax | — | 30.0 | — | — | — | — |
| Tricalcium Phosphate | 10.0 | 10.0 | 5.0 | 5.0 | 5.0 | 5.0 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 12

|  | Example 66 | Example 67 | Example 68 | Example 69 | Example 70 | Example 71 |
|---|---|---|---|---|---|---|
| Carnauba Wax | — | — | — | — | — | — |
| Candelilla Wax | 2.0 | 0.2 | — | — | — | — |
| Rice Bran Wax | — | — | 2.0 | 0.2 | — | — |
| Beeswax | — | — | — | — | 2.0 | 0.2 |
| Japan Wax | — | — | — | — | — | — |
| Tricalcium Phosphate | 5.0 | 5.0 | 5.0 | 5.0 | 5.0 | 5.0 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 13

|  | Example 72 | Example 73 | Example 74 | Example 75 | Example 76 | Example 77 |
|---|---|---|---|---|---|---|
| Carnauba Wax | — | — | 5.0 | — | — | — |
| Candelilla Wax | — | — | — | 0.02 | — | — |
| Rice Bran Wax | — | — | — | — | 0.0001 | — |
| Beeswax | — | — | — | — | — | 30.0 |
| Japan Wax | 0.2 | 0.02 | — | — | — | — |
| Tricalcium Phosphate | 5.0 | 5.0 | 1.0 | 1.0 | 1.0 | 1.0 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |

TABLE 13-continued

|  | Example 72 | Example 73 | Example 74 | Example 75 | Example 76 | Example 77 |
|---|---|---|---|---|---|---|
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 14

|  | Example 78 | Example 79 | Example 80 | Example 81 | Example 82 | Example 83 |
|---|---|---|---|---|---|---|
| Carnauba Wax | — | 10.0 | — | — | 0.2 | — |
| Candelilla Wax | — | — | 2.0 | — | — | 5.0 |
| Rice Bran Wax | — | — | — | — | — | — |
| Beeswax | — | — | — | 5.0 | — | — |
| Japan Wax | 0.0001 | — | — | — | — | — |
| Tricalcium Phosphate | 1.0 | 0.1 | 0.1 | 0.1 | 0.01 | 0.01 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 15

|  | Example 84 | Example 85 | Example 86 | Example 87 | Example 88 |
|---|---|---|---|---|---|
| Carnauba Wax | 0.0001 | — | — | 0.1 | 0.01 |
| Candelilla Wax | — | 30.0 | — | 0.05 | — |
| Rice Bran Wax | — | — | — | — | 0.01 |
| Beeswax | — | — | — | 0.05 | — |
| Japan Wax | — | — | 5.0 | — | — |
| Tricalcium Phosphate | 0.001 | 0.001 | 0.001 | 10.0 | 10.0 |
| Glycerin | 20.0 | 20.0 | 20.0 | 20.0 | 20.0 |
| Carboxymethyl Cellulose | 2.0 | 2.0 | 2.0 | 2.0 | 2.0 |
| Silica | 5.0 | 5.0 | 5.0 | 5.0 | 5.0 |
| Polyethylene Glycol | 3.0 | 3.0 | 3.0 | 3.0 | 3.0 |
| Sodium Lauryl Sulfate | 1.0 | 1.0 | 1.0 | 1.0 | 1.0 |
| Cetylpyridinium Chloride | 0.1 | 0.1 | 0.1 | 0.1 | 0.1 |
| Menthol | 0.5 | 0.5 | 0.5 | 0.5 | 0.5 |
| Purified Water | Balance | Balance | Balance | Balance | Balance |
| Total | 100.0 | 100.0 | 100.0 | 100.0 | 100.0 |

TABLE 16

|  | Example 89 | Example 90 | Example 91 | Example 92 | Example 93 | Example 94 |
|---|---|---|---|---|---|---|
| Carnauba Wax | 0.0001 | — | — | — | — | 0.02 |
| Candelilla Wax | — | 30.0 | — | 10.0 | — | — |
| Rice Bran Wax | — | — | — | — | — | — |
| Beeswax | — | — | — | — | — | — |
| Japan Wax | — | — | 5.0 | — | 30.0 | — |
| Calcium Monohydrogen Phosphate | 30.0 | 30.0 | 30.0 | 20.0 | 20.0 | 10.0 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |

TABLE 16-continued

|  | Example 89 | Example 90 | Example 91 | Example 92 | Example 93 | Example 94 |
|---|---|---|---|---|---|---|
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 17

|  | Example 95 | Example 96 | Example 97 | Example 98 | Example 99 | Example 100 |
|---|---|---|---|---|---|---|
| Carnauba Wax | — | 30.0 | 2.0 | 0.2 | — | — |
| Candelilla Wax | — | — | — | — | 5.0 | 0.2 |
| Rice Bran Wax | — | — | — | — | — | — |
| Beeswax | 0.0001 | — | — | — | — | — |
| Japan Wax | — | — | — | — | — | — |
| Calcium Monohydrogen Phosphate | 10.0 | 5.0 | 5.0 | 5.0 | 5.0 | 5.0 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 18

|  | Example 101 | Example 102 | Example 103 | Example 104 | Example 105 | Example 106 |
|---|---|---|---|---|---|---|
| Carnauba Wax | — | — | — | — | — | — |
| Candelilla Wax | 0.02 | — | — | — | — | — |
| Rice Bran Wax | — | 0.2 | 0.02 | — | — | — |
| Beeswax | — | — | — | 2.0 | 0.02 | — |
| Japan Wax | — | — | — | — | — | 2.0 |
| Calcium Monohydrogen Phosphate | 5.0 | 5.0 | 5.0 | 5.0 | 5.0 | 5.0 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 19

|  | Example 107 | Example 108 | Example 109 | Example 110 | Example 111 | Example 112 |
|---|---|---|---|---|---|---|
| Carnauba Wax | — | 10.0 | — | — | — | — |
| Candelilla Wax | — | — | 2.0 | — | — | — |
| Rice Bran Wax | — | — | — | 0.0001 | — | — |
| Beeswax | — | — | — | — | 30.0 | — |
| Japan Wax | 0.2 | — | — | — | — | 0.0001 |
| Calcium Monohydrogen Phosphate | 5.0 | 1.0 | 1.0 | 1.0 | 1.0 | 1.0 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 20

|  | Example 113 | Example 114 | Example 115 | Example 116 | Example 117 | Example 118 |
|---|---|---|---|---|---|---|
| Carnauba Wax | 5.0 | — | — | 0.2 | — | 30.0 |
| Candelilla Wax | — | 0.02 | — | — | — | — |
| Rice Bran Wax | — | — | 30.0 | — | 5.0 | — |
| Beeswax | — | — | — | — | — | — |
| Japan Wax | — | — | — | — | — | — |
| Calcium Monohydrogen Phosphate | 0.1 | 0.1 | 0.1 | 0.01 | 0.01 | 0.001 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 21

|  | Example 119 | Example 120 | Example 121 | Example 122 | Example 123 |
|---|---|---|---|---|---|
| Carnauba Wax | — | — | — | 0.005 | — |
| Candelilla Wax | 0.0001 | — | 0.1 | 0.005 | — |
| Rice Bran Wax | — | — | — | — | — |
| Beeswax | — | 5.0 | — | 0.005 | 1.0 |
| Japan Wax | — | — | 0.1 | 0.005 | 1.0 |
| Calcium Monohydrogen Phosphate | 0.001 | 0.001 | 30.0 | 30.0 | 30.0 |
| Glycerin | 20.0 | 20.0 | 20.0 | 20.0 | 20.0 |
| Carboxymethyl Cellulose | 2.0 | 2.0 | 2.0 | 2.0 | 2.0 |
| Silica | 5.0 | 5.0 | 5.0 | 5.0 | 5.0 |
| Polyethylene Glycol | 3.0 | 3.0 | 3.0 | 3.0 | 3.0 |
| Sodium Lauryl Sulfate | 1.0 | 1.0 | 1.0 | 1.0 | 1.0 |
| Cetylpyridinium Chloride | 0.1 | 0.1 | 0.1 | 0.1 | 0.1 |
| Menthol | 0.5 | 0.5 | 0.5 | 0.5 | 0.5 |
| Purified Water | Balance | Balance | Balance | Balance | Balance |
| Total | 100.0 | 100.0 | 100.0 | 100.0 | 100.0 |

TABLE 22

|  | Comparative Example 1 | Comparative Example 2 | Comparative Example 3 | Comparative Example 4 | Comparative Example 5 | Comparative Example 6 |
|---|---|---|---|---|---|---|
| Carnauba Wax | 0.0001 | 0.001 | 0.02 | 0.2 | 2.0 | 5.0 |
| Candelilla Wax | — | — | — | — | — | — |
| Rice Bran Wax | — | — | — | — | — | — |
| Beeswax | — | — | — | — | — | — |
| Japan Wax | — | — | — | — | — | — |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 23

|  | Comparative Example 7 | Comparative Example 8 | Comparative Example 9 | Comparative Example 10 | Comparative Example 11 | Comparative Example 12 |
|---|---|---|---|---|---|---|
| Carnauba Wax | 10.0 | 20.0 | 30.0 | — | — | — |
| Candelilla Wax | — | — | — | 0.0001 | 0.001 | 0.02 |
| Rice Bran Wax | — | — | — | — | — | — |
| Beeswax | — | — | — | — | — | — |
| Japan Wax | — | — | — | — | — | — |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 24

|  | Comparative Example 13 | Comparative Example 14 | Comparative Example 15 | Comparative Example 16 | Comparative Example 17 | Comparative Example 18 |
|---|---|---|---|---|---|---|
| Carnauba Wax | — | — | — | — | — | — |
| Candelilla Wax | 0.2 | 2.0 | 5.0 | 10.0 | 20.0 | 30.0 |
| Rice Bran Wax | — | — | — | — | — | — |
| Beeswax | — | — | — | — | — | — |
| Japan Wax | — | — | — | — | — | — |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |

TABLE 24-continued

|  | Comparative Example 13 | Comparative Example 14 | Comparative Example 15 | Comparative Example 16 | Comparative Example 17 | Comparative Example 18 |
|---|---|---|---|---|---|---|
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 25

|  | Comparative Example 19 | Comparative Example 20 | Comparative Example 21 | Comparative Example 22 | Comparative Example 23 | Comparative Example 24 |
|---|---|---|---|---|---|---|
| Carnauba Wax | — | — | — | — | — | — |
| Candelilla Wax | — | — | — | — | — | — |
| Rice Bran Wax | 0.0001 | 0.001 | 0.02 | 0.2 | 2.0 | 5.0 |
| Beeswax | — | — | — | — | — | — |
| Japan Wax | — | — | — | — | — | — |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 26

|  | Comparative Example 25 | Comparative Example 26 | Comparative Example 27 | Comparative Example 28 | Comparative Example 29 | Comparative Example 30 |
|---|---|---|---|---|---|---|
| Carnauba Wax | — | — | — | — | — | — |
| Candelilla Wax | — | — | — | — | — | — |
| Rice Bran Wax | 10.0 | 20.0 | 30.0 | — | — | — |
| Beeswax | — | — | — | 0.0001 | 0.001 | 0.02 |
| Japan Wax | — | — | — | — | — | — |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 27

| | Comparative Example 31 | Comparative Example 32 | Comparative Example 33 | Comparative Example 34 | Comparative Example 35 | Comparative Example 36 |
|---|---|---|---|---|---|---|
| Carnauba Wax | — | — | — | — | — | — |
| Candelilla Wax | — | — | — | — | — | — |
| Rice Bran Wax | — | — | — | — | — | — |
| Beeswax | 0.2 | 2.0 | 5.0 | 10.0 | 20.0 | 30.0 |
| Japan Wax | — | — | — | — | — | — |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 28

| | Comparative Example 37 | Comparative Example 38 | Comparative Example 39 | Comparative Example 40 | Comparative Example 41 | Comparative Example 42 |
|---|---|---|---|---|---|---|
| Carnauba Wax | — | — | — | — | — | — |
| Candelilla Wax | — | — | — | — | — | — |
| Rice Bran Wax | — | — | — | — | — | — |
| Beeswax | — | — | — | — | — | — |
| Japan Wax | 0.0001 | 0.001 | 0.02 | 0.2 | 2.0 | 5.0 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 29

| | Comparative Example 43 | Comparative Example 44 | Comparative Example 45 |
|---|---|---|---|
| Carnauba Wax | — | — | — |
| Candelilla Wax | — | — | — |
| Rice Bran Wax | — | — | — |
| Beeswax | — | — | — |
| Japan Wax | 10.0 | 20.0 | 30.0 |
| Glycerin | 20.0 | 20.0 | 20.0 |
| Carboxymethyl Cellulose | 2.0 | 2.0 | 2.0 |
| Silica | 5.0 | 5.0 | 5.0 |
| Polyethylene Glycol | 3.0 | 3.0 | 3.0 |
| Sodium Lauryl Sulfate | 1.0 | 1.0 | 1.0 |
| Cetylpyridinium Chloride | 0.1 | 0.1 | 0.1 |
| Menthol | 0.5 | 0.5 | 0.5 |
| Purified Water | Balance | Balance | Balance |
| Total | 100.0 | 100.0 | 100.0 |

TABLE 30

| | Comparative Example 46 | Comparative Example 47 | Comparative Example 48 | Comparative Example 49 | Comparative Example 50 | Comparative Example 51 |
|---|---|---|---|---|---|---|
| Hydroxyapatite | 0.001 | 0.01 | 0.1 | 1.0 | 5.0 | 10.0 |
| Tricalcium Phosphate | — | — | — | — | — | — |
| Calcium Monohydrogen Phosphate | | | | | | |

TABLE 30-continued

|  | Comparative Example 46 | Comparative Example 47 | Comparative Example 48 | Comparative Example 49 | Comparative Example 50 | Comparative Example 51 |
|---|---|---|---|---|---|---|
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 31

|  | Comparative Example 52 | Comparative Example 53 | Comparative Example 54 | Comparative Example 55 | Comparative Example 56 | Comparative Example 57 |
|---|---|---|---|---|---|---|
| Hydroxyapatite | 20.0 | 30.0 | 35.0 | — | — | — |
| Tricalcium Phosphate | — | — | — | 0.001 | 0.01 | 0.1 |
| Calcium Monohydrogen Phosphate | — | — | — | — | — | — |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 32

|  | Comparative Example 58 | Comparative Example 59 | Comparative Example 60 | Comparative Example 61 | Comparative Example 62 | Comparative Example 63 |
|---|---|---|---|---|---|---|
| Hydroxyapatite | — | — | — | — | — | — |
| Tricalcium Phosphate | 1.0 | 5.0 | 10.0 | 30.0 | 35.0 | — |
| Calcium Monohydrogen Phosphate | — | — | — | — | — | 0.001 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 33

|  | Comparative Example 64 | Comparative Example 65 | Comparative Example 66 | Comparative Example 67 | Comparative Example 68 | Comparative Example 69 |
|---|---|---|---|---|---|---|
| Hydroxyapatite | — | — | — | — | — | — |
| Tricalcium Phosphate | — | — | — | — | — | — |
| Calcium Monohydrogen Phosphate | 0.01 | 0.1 | 1.0 | 5.0 | 10.0 | 20.0 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

TABLE 34

|  | Comparative Example 70 | Comparative Example 71 |
|---|---|---|
| Hydroxyapatite | — | — |
| Tricalcium Phosphate | — | — |
| Calcium Monohydrogen Phosphate | 30.0 | 35.0 |
| Glycerin | 20.0 | 20.0 |
| Carboxymethyl Cellulose | 2.0 | 2.0 |
| Silica | 5.0 | 5.0 |
| Polyethylene Glycol | 3.0 | 3.0 |
| Sodium Lauryl Sulfate | 1.0 | 1.0 |
| Cetylpyridinium Chloride | 0.1 | 0.1 |
| Menthol | 0.5 | 1.0 |
| Purified Water | Balance | Balance |
| Total | 100.0 | 100.0 |

TABLE 35

|  | Comparative Example 72 | Comparative Example 73 | Comparative Example 74 | Comparative Example 75 | Comparative Example 76 | Comparative Example 77 |
|---|---|---|---|---|---|---|
| Carnauba Wax | 0.2 | — | — | — | 2.0 | — |
| Candelilla Wax | — | — | 0.2 | — | — | 0.2 |
| Rice Bran Wax | — | 1.0 | — | — | — | — |
| Beeswax | — | — | — | 1.0 | — | — |
| Japan Wax | — | — | — | — | — | — |
| Hydroxyapatite | 35.0 | 35.0 | — | — | — | — |
| Tricalcium Phosphate | — | — | 35.0 | 35.0 | — | — |
| Calcium Monohydrogen Phosphate | — | — | — | — | 35.0 | 35.0 |
| Glycerin | 20.0 | 20.0 | 20.0 | 20.0 | 20.0 | 20.0 |
| Carboxymethyl Cellulose | 2.0 | 2.0 | 2.0 | 2.0 | 2.0 | 2.0 |
| Silica | 5.0 | 5.0 | 5.0 | 5.0 | 5.0 | 5.0 |
| Polyethylene Glycol | 3.0 | 3.0 | 3.0 | 3.0 | 3.0 | 3.0 |
| Sodium Lauryl Sulfate | 1.0 | 1.0 | 1.0 | 1.0 | 1.0 | 1.0 |
| Cetylpyridinium Chloride | 0.1 | 0.1 | 0.1 | 0.1 | 0.1 | 0.1 |
| Menthol | 0.5 | 0.5 | 0.5 | 0.5 | 0.5 | 0.5 |
| Purified Water | Balance | Balance | Balance | Balance | Balance | Balance |
| Total | 100.0 | 100.0 | 100.0 | 100.0 | 100.0 | 100.0 |

2. Liquid Dentifrice

TABLE 36

|  | Example 124 | Example 125 | Example 126 | Example 127 | Example 128 | Example 129 |
|---|---|---|---|---|---|---|
| Carnauba Wax | — | — | — | — | 2.0 | — |
| Candelilla Wax | 0.0001 | 0.2 | — | — | — | — |
| Rice Bran Wax | — | — | — | — | — | 2.0 |
| Beeswax | — | — | 0.02 | — | — | — |
| Japan Wax | — | — | — | 0.001 | — | — |
| Hydroxyapatite | 10.0 | 5.0 | 1.0 | 0.1 | 0.001 | — |
| Tricalcium Phosphate | — | — | — | — | — | 10.0 |
| Calcium Monohydrogen Phosphate | — | — | — | — | — | — |
| Xylitol | 10.0 | 10.0 | 10.0 | 10.0 | 10.0 | 10.0 |
| Carrageenan | 1.0 | 1.0 | 1.0 | 1.0 | 1.0 | 1.0 |
| Glycerin | 10.0 | 10.0 | 10.0 | 10.0 | 10.0 | 10.0 |
| Menthol | 0.4 | 0.4 | 0.4 | 0.4 | 0.4 | 0.4 |
| Purified Water | Balance | Balance | Balance | Balance | Balance | Balance |
| Total | 100.0 | 100.0 | 100.0 | 100.0 | 100.0 | 100.0 |

TABLE 37

|  | Example 130 | Example 131 | Example 132 | Example 133 | Example 134 | Example 135 |
|---|---|---|---|---|---|---|
| Carnauba Wax | 0.001 | — | — | — | — | 0.02 |
| Candelilla Wax | — | 2.0 | — | — | — | — |
| Rice Bran Wax | — | — | — | — | 0.0001 | — |
| Beeswax | — | — | — | 0.0001 | — | — |
| Japan Wax | — | — | 0.2 | — | — | — |
| Hydroxyapatite | — | — | — | — | — | — |
| Tricalcium Phosphate | 5.0 | 0.1 | 0.01 | 0.001 | — | — |
| Calcium Monohydrogen Phosphate | — | — | — | — | 1.0 | 0.01 |
| Xylitol | 10.0 | 10.0 | 10.0 | 10.0 | 10.0 | 10.0 |
| Carrageenan | 1.0 | 1.0 | 1.0 | 1.0 | 1.0 | 1.0 |
| Glycerin | 10.0 | 10.0 | 10.0 | 10.0 | 10.0 | 10.0 |
| Menthol | 0.4 | 0.4 | 0.4 | 0.4 | 0.4 | 0.4 |
| Purified Water | Balance | Balance | Balance | Balance | Balance | Balance |
| Total | 100.0 | 100.0 | 100.0 | 100.0 | 100.0 | 100.0 |

TABLE 38

|  | Comparative Example 78 | Comparative Example 79 | Comparative Example 80 | Comparative Example 81 | Comparative Example 82 | Comparative Example 83 |
|---|---|---|---|---|---|---|
| Carnauba Wax | 0.001 | 0.02 | 2.0 | — | — | — |
| Candelilla Wan | — | — | — | 0.0001 | 0.2 | 2.0 |
| Rice Bran Wax | — | — | — | — | — | — |
| Beeswax | — | — | — | — | — | — |
| Japan Wax | — | — | — | — | — | — |
| Xylitol | 10.0 | 10.0 | 10.0 | 10.0 | 10.0 | 10.0 |
| Carrageenan | 1.0 | 1.0 | 1.0 | 1.0 | 1.0 | 1.0 |
| Glycerin | 10.0 | 10.0 | 10.0 | 10.0 | 10.0 | 10.0 |
| Menthol | 0.4 | 0.4 | 0.4 | 0.4 | 0.4 | 0.4 |
| Purified Water | Balance | Balance | Balance | Balance | Balance | Balance |
| Total | 100.0 | 100.0 | 100.0 | 100.0 | 100.0 | 100.0 |

TABLE 39

| | Comparative Example 84 | Comparative Example 85 | Comparative Example 86 | Comparative Example 87 | Comparative Example 88 | Comparative Example 89 |
|---|---|---|---|---|---|---|
| Carnauba Wax | — | — | — | — | — | — |
| Candelilla Wax | — | — | — | — | — | — |
| Rice Bran Wax | 0.0001 | 2.0 | — | — | — | — |
| Beeswax | — | — | 0.0001 | 0.02 | — | — |
| Japan Wax | — | — | — | — | 0.001 | 0.2 |
| Xylitol | 10.0 | 10.0 | 10.0 | 10.0 | 10.0 | 10.0 |
| Carrageenan | 1.0 | 1.0 | 1.0 | 1.0 | 1.0 | 1.0 |
| Glycerin | 10.0 | 10.0 | 10.0 | 10.0 | 10.0 | 10.0 |
| Menthol | 0.4 | 0.4 | 0.4 | 0.4 | 0.4 | 0.4 |
| Purified Water | Balance | Balance | Balance | Balance | Balance | Balance |
| Total | 100.0 | 100.0 | 100.0 | 100.0 | 100.0 | 100.0 |

TABLE 40

| | Comparative Example 90 | Comparative Example 91 | Comparative Example 92 | Comparative Example 93 | Comparative Example 94 | Comparative Example 95 |
|---|---|---|---|---|---|---|
| Hydroxyapatite | 10.0 | 5.0 | 1.0 | 0.1 | 0.001 | — |
| Tricalcium Phosphate | — | — | — | — | — | 10.0 |
| Calcium Monohydrogen Phosphate | — | — | — | — | — | — |
| Xylitol | 10.0 | 10.0 | 10.0 | 10.0 | 10.0 | 10.0 |
| Carrageenan | 1.0 | 1.0 | 1.0 | 1.0 | 1.0 | 1.0 |
| Glycerin | 10.0 | 10.0 | 10.0 | 10.0 | 10.0 | 10.0 |
| Menthol | 0.4 | 0.4 | 0.4 | 0.4 | 0.4 | 0.4 |
| Purified Water | Balance | Balance | Balance | Balance | Balance | Balance |
| Total | 100.0 | 100.0 | 100.0 | 100.0 | 100.0 | 100.0 |

TABLE 41

| | Comparative Example 96 | Comparative Example 97 | Comparative Example 98 | Comparative Example 99 | Comparative Example 100 | Comparative Example 101 |
|---|---|---|---|---|---|---|
| Hydroxyapatite | — | — | — | — | — | — |
| Tricalcium Phosphate | 5.0 | 0.1 | 0.01 | 0.001 | — | — |
| Calcium Monohydrogen Phosphate | — | — | — | — | 1.0 | 0.01 |
| Xylitol | 10.0 | 10.0 | 10.0 | 10.0 | 10.0 | 10.0 |
| Carrageenan | 1.0 | 1.0 | 1.0 | 1.0 | 1.0 | 1.0 |
| Glycerin | 10.0 | 10.0 | 10.0 | 10.0 | 10.0 | 10.0 |
| Menthol | 0.4 | 0.4 | 0.4 | 0.4 | 0.4 | 0.4 |
| Purified Water | Balance | Balance | Balance | Balance | Balance | Balance |
| Total | 100.0 | 100.0 | 100.0 | 100.0 | 100.0 | 100.0 |

[Remineralization Test Method]

To confirm a remineralizing effect, a pre-prepared artificial incipient caries test sample was used. The coronal labial surface enamel of bovine front teeth was used for the preparation of the artificial incipient caries test sample. The enamel surface was abraded using #1000, #2400, and #4000 abrasive papers. The part to be tested of the abraded enamel surface was subjected to the preparation of an about 5×3 mm window using Nail Enamel (from Shiseido Co., Ltd.) and immersed in a 0.1 M lactate buffer solution (pH 4.8, 3.0 mmM $CaCl_2$, 1.8 mmM $KH_2PO_4$, 1.0% CMC) at 37° C. for 4 days to prepare artificial incipient caries. For a test control, one-half of the side of the coronal crown in the about 5×3 mm window was further masked using Nail Enamel (from Shiseido Co., Ltd.) to make a part to be compared (control). The toothpaste and the liquid dentifrice were each mixed with purified water to make a suspended solution, which was used as a test solution (a material to be tested).

For a remineralization test, the artificial incipient caries test body prepared above was immersed in each test solution for 12 days; the test body was then cut to a thickness of about 500 μm so as to be parallel with the tooth axis using a micro cutter; and thereafter, the section was abraded to a parallel thin section having a thickness of about 100 μm under watering using #1000, #2400, and #4000 abrasive papers.

After abrasion, to confirm a tooth-remineralizing effect, contact micro radiograph (CMR) photographing was carried out (see FIGS. 1 and 2). The "control surface" in each figure is a part to be compared to know the extent to which the tooth-cleaning compositions in Examples and Comparative Examples have a remineralizing effect, and is one maintaining the state of artificial incipient caries. The part is the half part of the artificial incipient caries (about 5×3 mm window)

area. The "treated surface" in each figure is a part exposed to test solutions (materials to be tested) in Examples and Comparative Examples.

The remineralizing effect in the artificial incipient caries part was analyzed using a computer.

In an image analysis using the computer, the amount of the remineralized mineral was calculated based on the equation of Angmer et al. (B. Angmer, D. Carlstrom and J. E. Glas: Studies on Ultrastructure of Dental Enamel IV: The Mineralization of normal Human Enamel, J. Ultrastructure. Res. 8, 12-23, 1963), and the mineral loss amount $\Delta Z$ (% volume mineral·µm) in the control and treated surfaces of each section was calculated according to the method of Damato et al. (F. A. Damato, R. Stang and K. W. Stephen: Effect of Fluoride Concentration on Reminerelization of Carious Enamel: an in vitro pH-Cycling Study, Caries Res, 24, 174-180, 1990). The remineralization rate was calculated from the following equation.

$$\text{Remineralization Rate} = \frac{\Delta Z \text{ in Control Surface} - \Delta Z \text{ in Treated Surface}}{\Delta Z \text{ in Control Surface}} \times 100 (\%) \qquad \text{[Expression 1]}$$

Tables 42 to 45 shows the results of confirming the remineralizing effect of the tooth-cleaning compositions by the computer image analysis method.

1. Toothpaste

TABLE 42

| | Example | | | | | |
|---|---|---|---|---|---|---|
| | Example 1 | Example 2 | Example 3 | Example 4 | Example 5 | Example 6 |
| Remineralization Rate (%) | 17.7 | 16.3 | 16.5 | 15.9 | 20.3 | 17.4 |
| | Example | | | | | |
| | Example 7 | Example 8 | Example 9 | Example 10 | Example 11 | Example 12 |
| Remineralization Rate (%) | 16.8 | 21.7 | 31.9 | 27.6 | 41.8 | 20.8 |
| | Example | | | | | |
| | Example 13 | Example 14 | Example 15 | Example 16 | Example 17 | Example 18 |
| Remineralization Rate (%) | 19.1 | 17.0 | 25.2 | 18.3 | 24.9 | 34.6 |
| | Example | | | | | |
| | Example 19 | Example 20 | Example 21 | Example 22 | Example 23 | Example 24 |
| Remineralization Rate (%) | 39.1 | 23.8 | 17.3 | 18.0 | 26.1 | 30.1 |
| | Example | | | | | |
| | Example 25 | Example 26 | Example 27 | Example 28 | Example 29 | Example 30 |
| Remineralization Rate (%) | 18.2 | 31.4 | 31.5 | 28.2 | 25.8 | 26.1 |
| | Example | | | | | |
| | Example 31 | Example 32 | Example 33 | Example 34 | Example 35 | Example 36 |
| Remineralization Rate (%) | 24.1 | 19.1 | 20.1 | 24.1 | 24.3 | 16.2 |
| | Example | | | | | |
| | Example 37 | Example 38 | Example 39 | Example 40 | Example 41 | Example 42 |
| Remineralization Rate (%) | 16.4 | 23.0 | 15.5 | 26.8 | 34.0 | 12.3 |
| | Example | | | | | |
| | Example 43 | Example 44 | Example 45 | Example 46 | Example 47 | Example 48 |
| Remineralization Rate (%) | 16.1 | 10.7 | 9.1 | 9.3 | 8.6 | 22.4 |

TABLE 42-continued

| | Example | | | | | |
|---|---|---|---|---|---|---|
| | Example 49 | Example 50 | Example 51 | Example 52 | Example 53 | Example 54 |
| Remineralization Rate (%) | 15.1 | 12.6 | 23.1 | 34.1 | 27.6 | 11.3 |
| | Example | | | | | |
| | Example 55 | Example 56 | Example 57 | Example 58 | Example 59 | Example 60 |
| Remineralization Rate (%) | 10.9 | 15.4 | 32.4 | 15.1 | 13.0 | 11.5 |
| | Example | | | | | |
| | Example 61 | Example 62 | Example 63 | Example 64 | Example 65 | Example 66 |
| Remineralization Rate (%) | 12.6 | 18.0 | 29.5 | 17.2 | 11.3 | 21.0 |
| | Example | | | | | |
| | Example 67 | Example 68 | Example 69 | Example 70 | Example 71 | Example 72 |
| Remineralization Rate (%) | 24.2 | 26.1 | 24.0 | 21.1 | 19.7 | 21.1 |
| | Example | | | | | |
| | Example 73 | Example 74 | Example 75 | Example 76 | Example 77 | Example 78 |
| Remineralization Rate (%) | 18.5 | 25.1 | 18.8 | 17.5 | 9.4 | 11.1 |
| | Example | | | | | |
| | Example 79 | Example 80 | Example 81 | Example 82 | Example 83 | Example 84 |
| Remineralization Rate (%) | 15.5 | 18.5 | 17.8 | 26.1 | 13.2 | 7.2 |
| | Example | | | | | |
| | Example 85 | Example 86 | Example 87 | Example 88 | Example 89 | Example 90 |
| Remineralization Rate (%) | 7.6 | 12.0 | 28.8 | 21.5 | 5.9 | 6.0 |
| | Example | | | | | |
| | Example 91 | Example 92 | Example 93 | Example 94 | Example 95 | Example 96 |
| Remineralization Rate (%) | 6.3 | 9.5 | 8.0 | 11.5 | 7.5 | 6.5 |
| | Example | | | | | |
| | Example 97 | Example 98 | Example 99 | Example 100 | Example 101 | Example 102 |
| Remineralization Rate (%) | 28.8 | 26.4 | 10.8 | 18.0 | 13.8 | 18.8 |
| | Example | | | | | |
| | Example 103 | Example 104 | Example 105 | Example 106 | Example 107 | Example 108 |
| Remineralization Rate (%) | 17.8 | 16.5 | 11.7 | 14.7 | 15.1 | 12.5 |
| | Example | | | | | |
| | Example 109 | Example 110 | Example 111 | Example 112 | Example 113 | Example 114 |
| Remineralization Rate (%) | 14.5 | 13.5 | 6.2 | 7.0 | 22.0 | 13.3 |

TABLE 42-continued

| | Example | | | | | |
|---|---|---|---|---|---|---|
| | Example 115 | Example 116 | Example 117 | Example 118 | Example 119 | Example 120 |
| Remineralization Rate (%) | 6.6 | 25.8 | 18.0 | 5.9 | 5.6 | 14.3 |

| | Example | | |
|---|---|---|---|
| | Example 121 | Example 122 | Example 123 |
| Remineralization Rate (%) | 16.8 | 13.0 | 16.9 |

TABLE 43

| | Example | | | | | |
|---|---|---|---|---|---|---|
| | Comparative Example 1 | Comparative Example 2 | Comparative Example 3 | Comparative Example 4 | Comparative Example 5 | Comparative Example 6 |
| Remineralization Rate (%) | 1.4 | 0.8 | 0.9 | 0.3 | 0.3 | 0.8 |

| | Example | | | | | |
|---|---|---|---|---|---|---|
| | Comparative Example 7 | Comparative Example 8 | Comparative Example 9 | Comparative Example 10 | Comparative Example 11 | Comparative Example 12 |
| Remineralization Rate (%) | 1.3 | 1.1 | 1.1 | 1.3 | 1.0 | 0.3 |

| | Example | | | | | |
|---|---|---|---|---|---|---|
| | Comparative Example 13 | Comparative Example 14 | Comparative Example 15 | Comparative Example 16 | Comparative Example 17 | Comparative Example 18 |
| Remineralization Rate (%) | 0.9 | 0.6 | 1.0 | 0.2 | 1.1 | 0.7 |

| | Example | | | | | |
|---|---|---|---|---|---|---|
| | Comparative Example 19 | Comparative Example 20 | Comparative Example 21 | Comparative Example 22 | Comparative Example 23 | Comparative Example 24 |
| Remineralization Rate (%) | 0.8 | 0.3 | 0.2 | 0.3 | 1.2 | 0.6 |

| | Example | | | | | |
|---|---|---|---|---|---|---|
| | Comparative Example 25 | Comparative Example 26 | Comparative Example 27 | Comparative Example 28 | Comparative Example 29 | Comparative Example 30 |
| Remineralization Rate (%) | 1.1 | 0.7 | 1.6 | 0.4 | 1.6 | 1.5 |

| | Example | | | | | |
|---|---|---|---|---|---|---|
| | Comparative Example 31 | Comparative Example 32 | Comparative Example 33 | Comparative Example 34 | Comparative Example 35 | Comparative Example 36 |
| Remineralization Rate (%) | 0.7 | 0.3 | 1.3 | 0.8 | 0.5 | 0.4 |

TABLE 43-continued

|  | Example | | | | | |
| --- | --- | --- | --- | --- | --- | --- |
|  | Comparative Example 37 | Comparative Example 38 | Comparative Example 39 | Comparative Example 40 | Comparative Example 41 | Comparative Example 42 |
| Remineralization Rate (%) | 0.5 | 0.7 | 1.6 | 0.7 | 0.3 | 0.4 |

|  | Example | | |
| --- | --- | --- | --- |
|  | Comparative Example 43 | Comparative Example 44 | Comparative Example 45 |
| Remineralization Rate (%) | 1.0 | 1.2 | 1.3 |

|  | Example | | | | | |
| --- | --- | --- | --- | --- | --- | --- |
|  | Comparative Example 46 | Comparative Example 47 | Comparative Example 48 | Comparative Example 49 | Comparative Example 50 | Comparative Example 51 |
| Remineralization Rate (%) | 2.8 | 5.0 | 8.0 | 9.1 | 10.6 | 11.1 |

|  | Example | | | | | |
| --- | --- | --- | --- | --- | --- | --- |
|  | Comparative Example 52 | Comparative Example 53 | Comparative Example 54 | Comparative Example 55 | Comparative Example 56 | Comparative Example 57 |
| Remineralization Rate (%) | 12.2 | 13.8 | 14.2 | 1.8 | 2.0 | 3.2 |

|  | Example | | | | | |
| --- | --- | --- | --- | --- | --- | --- |
|  | Comparative Example 58 | Comparative Example 59 | Comparative Example 60 | Comparative Example 61 | Comparative Example 62 | Comparative Example 63 |
| Remineralization Rate (%) | 4.5 | 6.4 | 7.1 | 7.8 | 7.7 | 1.2 |

|  | Example | | | | | |
| --- | --- | --- | --- | --- | --- | --- |
|  | Comparative Example 64 | Comparative Example 65 | Comparative Example 66 | Comparative Example 67 | Comparative Example 68 | Comparative Example 69 |
| Remineralization Rate (%) | 1.5 | 1.2 | 1.4 | 2.3 | 2.5 | 2.5 |

|  | Example | |
| --- | --- | --- |
|  | Comparative Example 70 | Comparative Example 71 |
| Remineralization Rate (%) | 2.7 | 2.7 |

|  | Example | | | | | |
| --- | --- | --- | --- | --- | --- | --- |
|  | Comparative Example 72 | Comparative Example 73 | Comparative Example 74 | Comparative Example 75 | Comparative Example 76 | Comparative Example 77 |
| Remineralization Rate (%) | 15.2 | 15.7 | 8.9 | 9.1 | 3.5 | 2.9 |

2. Liquid Dentifrice

TABLE 44

|  | Example | | | | | |
| --- | --- | --- | --- | --- | --- | --- |
|  | Example 124 | Example 125 | Example 126 | Example 127 | Example 128 | Example 129 |
| Remineralization Rate (%) | 16.6 | 30.2 | 21.3 | 17.8 | 33.1 | 28.2 |

TABLE 44-continued

|  | Example | | | | | |
| --- | --- | --- | --- | --- | --- | --- |
|  | Example 130 | Example 131 | Example 132 | Example 133 | Example 134 | Example 135 |
| Remineralization Rate (%) | 15.0 | 18.5 | 17.3 | 6.7 | 13.5 | 11.2 |

TABLE 45

| | Example | | | | | |
|---|---|---|---|---|---|---|
| | Comparative Example 78 | Comparative Example 79 | Comparative Example 80 | Comparative Example 81 | Comparative Example 82 | Comparative Example 83 |
| Remineralization Rate (%) | 0.7 | 1.0 | 1.3 | 0.8 | 1.2 | 0.4 |

| | Example | | | | | |
|---|---|---|---|---|---|---|
| | Comparative Example 84 | Comparative Example 85 | Comparative Example 86 | Comparative Example 87 | Comparative Example 88 | Comparative Example 89 |
| Remineralization Rate (%) | 0.5 | 1.0 | 0.6 | 0.4 | 0.9 | 1.1 |

| | Example | | | | | |
|---|---|---|---|---|---|---|
| | Comparative Example 90 | Comparative Example 91 | Comparative Example 92 | Comparative Example 93 | Comparative Example 94 | Comparative Example 95 |
| Remineralization Rate (%) | 11.0 | 10.0 | 9.6 | 8.2 | 4.8 | 6.7 |

| | Example | | | | | |
|---|---|---|---|---|---|---|
| | Comparative Example 96 | Comparative Example 97 | Comparative Example 98 | Comparative Example 99 | Comparative Example 100 | Comparative Example 101 |
| Remineralization Rate (%) | 6.8 | 3.1 | 2.2 | 2.3 | 1.7 | 1.8 |

As shown in Comparative Examples 1 to 45 and 78 to 89, various wax compositions alone had little tooth-remineralizing effect.

In contrast, compared to the use of hydroxyapatite, tricalcium phosphate, or calcium monohydrogen phosphate without any wax as shown in Comparative Examples 46 to 71 and 90 to 101, the addition of any of the waxes had a synergistically enhanced tooth-remineralizing effect. The total remineralization rate described below is a sum of remineralization rates in Comparative Examples for each comparison.

Specifically, the synergistic effect is evident from the comparisons, for example, between:

Example 9 (remineralization rate: 31.9%) and Comparative Examples 13 and 52 (total remineralization rate: 13.1%), Example 26 (remineralization rate: 31.4%) and Comparative Examples 23 and 50 (total remineralization rate: 11.8%), Example 37 (remineralization rate: 16.4%) and Comparative Examples 37 and 49 (total remineralization rate: 9.6%), Example 49 (remineralization rate: 15.1%) and Comparative Examples 34 and 46 (total remineralization rate: 3.6%), Example 58 (remineralization rate: 15.1%) and Comparative Examples 16 and 60 (total remineralization rate: 7.3%), Example 76 (remineralization rate: 17.5%) and Comparative Examples 19 and 58 (total remineralization rate: 5.3%), Example 82 (remineralization rate: 26.1%) and Comparative Examples 4 and 56 (total remineralization rate: 2.3%), Example 93 (remineralization rate: 8.0%) and Comparative Examples 45 and 69 (total remineralization rate: 3.8%), Example 105 (remineralization rate: 11.7%) and Comparative Examples 30 and 67 (total remineralization rate: 3.8%), Example 108 (remineralization rate: 12.5%) and Comparative Examples 7 and 66 (total remineralization rate: 2.7%), Example 128 (remineralization rate: 33.1%) and Comparative Examples 80 and 94 (total remineralization rate: 6.1%), Example 131 (remineralization rate: 18.5%) and Comparative Examples 83 and 97 (total remineralization rate: 3.5%), and Example 134 (remineralization rate: 13.5%) and Comparative Examples 84 and 100 (total remineralization rate: 2.2%).

However, the incorporation of each wax in one of the dentifrices shown in Comparative Examples 72 to 77, which contained the calcium phosphates in an amount of 35%, had no synergistic tooth-remineralizing effect compared to the incorporation of each calcium phosphate in an amount of 35% without any wax in the dentifrice.

INDUSTRIAL APPLICABILITY

The tooth-cleaning composition of the present invention is excellent in the remineralization of teeth, can be used in applications of various dentifrices, such as a toothpaste, a toothpowder, and a liquid dentifrice, and tooth remineralization in the oral cavity, and is high in industrial usefulness.

The invention claimed is:

1. A tooth-cleaning composition comprising a wax and a calcium phosphate, wherein a content of the calcium phosphate is 0.001 to 30% by mass and a content of the wax is 0.0001 to 30% by mass, wherein the combination of the content of the calcium phosphate and the content of the wax provide a synergistically enhanced tooth-remineralizing effect, and wherein the tooth-cleaning composition is a toothpaste, a toothpowder, or a liquid dentifrice.

2. The tooth-cleaning composition according to claim 1, wherein the calcium phosphate is at least one selected from the group consisting of hydroxyapatite, tricalcium phosphate, and calcium monohydrogen phosphate.

3. The tooth-cleaning composition according to claim 1, wherein the wax is at least one selected from the group consisting of shellac wax, Wang Li Guro, carnauba wax, sugar cane wax, bleached beeswax, bleached montan wax, rice bran wax, hydrogenated rice bran wax, spermaceti, deresin candelilla wax, candelilla wax, montan wax, paraffin wax, microcrystalline wax, Japan wax, oil seed wax, lanolin, beeswax, Chinese insect wax, and cane wax.

4. The tooth-cleaning composition according to claim 3, wherein the calcium phosphate is at least one selected from the group consisting of hydroxyapatite, tricalcium phosphate, and calcium monohydrogen phosphate.

5. The tooth-cleaning composition according to claim 2, wherein the wax is at least one selected from the group consisting of shellac wax, Wang Li Guro, carnauba wax, sugar cane wax, bleached beeswax, bleached montan wax, rice bran wax, hydrogenated rice bran wax, spermaceti, deresin candelilla wax, candelilla wax, montan wax, paraffin wax, microcrystalline wax, Japan wax, oil seed wax, lanolin, beeswax, Chinese insect wax, and cane wax.

* * * * *